US009572849B2

(12) United States Patent
Havkin-Frenkel

(10) Patent No.: US 9,572,849 B2
(45) Date of Patent: Feb. 21, 2017

(54) RECOVERY OF RESIDUAL PLANT COMPONENTS AFTER DISTILLATION OF ESSENTIAL OILS

(75) Inventor: Daphna Havkin-Frenkel, North Brunswick, NJ (US)

(73) Assignee: Bakto Natural Preservatives LLC, North Brunswick, NJ (US)

( * ) Notice: Subject to any disclaimer, the term of this patent is extended or adjusted under 35 U.S.C. 154(b) by 1200 days.

(21) Appl. No.: 11/793,641

(22) PCT Filed: Dec. 18, 2006

(86) PCT No.: PCT/US2006/048260
§ 371 (c)(1),
(2), (4) Date: May 8, 2008

(87) PCT Pub. No.: WO2007/075580
PCT Pub. Date: Jul. 5, 2007

(65) Prior Publication Data
US 2008/0254149 A1 Oct. 16, 2008

Related U.S. Application Data

(60) Provisional application No. 60/750,588, filed on Dec. 16, 2005.

(51) Int. Cl.
*A61K 36/534* (2006.01)
*A61K 36/28* (2006.01)
*A61K 36/282* (2006.01)
*A61K 36/53* (2006.01)
*A61K 36/537* (2006.01)

(52) U.S. Cl.
CPC ............ *A61K 36/534* (2013.01); *A61K 36/28* (2013.01); *A61K 36/282* (2013.01); *A61K 36/53* (2013.01); *A61K 36/537* (2013.01)

(58) Field of Classification Search
None
See application file for complete search history.

(56) References Cited

U.S. PATENT DOCUMENTS

| | | | | |
|---|---|---|---|---|
| 2,662,052 A | * | 12/1953 | Bridger et al. | 203/44 |
| 4,363,823 A | * | 12/1982 | Kimura | A23L 1/0107 252/398 |
| 5,026,550 A | * | 6/1991 | Aeschbach et al. | 424/746 |
| 5,525,260 A | * | 6/1996 | Aeschbach et al. | 252/398 |
| 6,383,543 B1 | * | 5/2002 | Reznik | 426/431 |
| 2003/0138537 A1 | * | 7/2003 | Bailey | A23B 4/20 426/542 |
| 2004/0175439 A1 | | 9/2004 | Cyr | |

FOREIGN PATENT DOCUMENTS

| | | | |
|---|---|---|---|
| JP | 59176385 A | * | 10/1984 |
| JP | 07330624 A | * | 12/1995 |
| JP | 08073337 A | * | 3/1996 |
| JP | 09208950 A | * | 8/1997 |

OTHER PUBLICATIONS

Kulisic et al. "Use of different methods for testing antioxidative activity of oregano essential oil". Food Chemistry, vol. 85 (2004) 633-640.*
Vekiari et al. "Oregano Flavonoids as Lipid Antioxidants". JAOCS, vol. 70, No. 5 (May 1993) 483-487.*
Madsen et al. "Screening of antioxidative activity of spices. A comparison between assays based on ESR spintrapping and electrochemical measurement of oxygen consumption" Food Chem, vol. 57, No. 2 (1996) 331-337.*
"Extraction Part 1". Internet Archive: Sep. 4, 2004 [Retrieved from the Internet on: Mar. 30, 2014]. Retrieved from: <URL: http://web.archive.org/web/20040904073555/http://www.chem.ucla.edu/~bacher/Specialtopics/extraction.html>.*
"How is coffee decaffeinated". Internet Archive Date: Jan. 19, 2000 [Retrieved from the Internet on: Dec. 8, 2014]. Retrieved from: <URL: https://web.archive.org/web/20000119174803/http://antoine.frostburg.edu/chem/senese/101/consumer/faq/decaffeinating-coffee.shtml>.*
Dudai, et al., "Monoterpene content in *Origanum syriacum* as affected by environmental conditions and flowering", *Physiologia Plantarum* (1992) 84:453-459.
International Preliminary Report on Patentability and Written Opinion of the International Searching Authority in PCT/US2006/048260, issued Jun. 18, 2008.

* cited by examiner

*Primary Examiner* — Amy L Clark
(74) *Attorney, Agent, or Firm* — Potter Anderson and Corroon LLP

(57) ABSTRACT

Methods for recovering valuable compounds and substances from plants after distillation of oils are disclosed. The methods involve various aqueous and non-aqueous solvent extraction of plant material from which oils have been distilled previously.

23 Claims, No Drawings

RECOVERY OF RESIDUAL PLANT COMPONENTS AFTER DISTILLATION OF ESSENTIAL OILS

This claims benefit of PCT/US2006/048260 filed Dec. 18, 2006 which claims priority to U.S. Provisional Application No. 60/750,588, filed Dec. 16, 2005, the entire contents of which are incorporated by reference herein.

FIELD OF THE INVENTION

The present invention is related to chemical and biological components derived from plants. In particular, the invention relates to a process for recovering substances from plant material residue after distillation of essential oils from the material.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Plants of a wide variety of species have been used for health promoting and particular medicinal purposes for many thousands of years. In recent years, research has revealed that plant-based phenols, flavonoids, isoflavones, terpenes, glucosinolates and other compounds present in fruits, vegetables and leafy herbs, among other types of plants, possess antioxidant and anti-carcinogenic properties, among other health-promoting benefits. Among certain aromatic herbs, such as mints and oregano, essential oils and extracts have been found to contain antiseptic, antimicrobial, anti-inflammatory and antiviral agents.

Due to the ever-growing consumer preference for natural products and remedies, the value of plant derived therapeutic agents has increased steadily. Moreover, the more traditional value base of certain plant components, e.g., for the flavor and fragrance industry, has remained robust.

Essential oils constitute one type of valuable plant component. An essential oil is a concentrated, hydrophobic liquid containing volatile aromatic compounds, obtained by distillation from various plant parts. Essential oils are used in perfumery, aromatherapy, cosmetics, incense, for flavoring food and drink, and in medicine. The medicinal value of certain essential oils can be considerable. For instance, the essential oils of oregano, which primarily contains carvacrol, thymol and p-cymene, is a powerful antibacterial and antimicrobial agent.

Essential oils are produced by water or steam distillation. Typically, the plant material is immersed in water and boiled, or exposed to steam flow. The steam and oil vapor is condensed and the oil is separated from the water. Customarily, the residual plant material is discarded once the essential oils have been distilled, on the assumption that the material would not yield additional components or substances of appreciable value once it has been subjected to the distillation process.

SUMMARY OF THE INVENTION

One aspect of the present invention features a method for obtaining one or more substances from plant material, comprising (a) providing post-distillation plant material that has previously been subjected to water or steam distillation of essential oils; (b) contacting the post-distillation plant material with a solvent under conditions permitting extraction of the one or more substances from the plant material into the solvent; and (c) obtaining the one or more substances from the solvent. The plant material may be from a whole plant or any plant part, including one or more of flowers, seeds, leaves, stems and roots. In certain embodiments, the plant material is composed of stems and leaves, and in an exemplary embodiment, leaves are utilized.

The plant material can be from any plant from which essential oils are extracted. In certain embodiments, the plant material is from a plant genus selected from *Origanum, Mentha, Agastache, Ocimum, Salvia, Artemisia, Melissa, Achillea, Thymus, Coridothymus, Micromeria, Rosmarinus, Pelargonium* and *Coleus*. In particular embodiments, the plant material is from *Mentha spicata, Mentha piperita, Rosmarinus officinalis, Origanum syriacum, Origanum dayi, Origanum vulgare, Thymus vulgare, Ocimum basilicum* or *Melissa officinalis*.

Substances that can be isolated in accordance with this method include but are not limited to phenolic compounds, flavones, isoflavones, glycosides, anthocyanins, proanthocyanidins, procyanidins, catechins, terpenes, lignins, tannins, glucosinilates, aliphatic and cyclic organic acids. In one embodiment, the one or more substances has antioxidant activity. In a particular embodiment, the method is adapted to favor extraction of phenolic compounds.

The solvent or solvent system can be of any type customarily used to extract substances such as those described herein from plant material. In one embodiment, the solvent is an alcohol. In a particular extraction the solvent is 80% ethanol. In embodiments utilizing a solvent that contains water, the method can further comprise removing the solvent from the water and extracting the remaining water with a different solvent, such as ethyl acetate.

In certain embodiments, the method further comprises extraction of the post-distillation plant material with another solvent. In one embodiment, the other solvent is a base, such as NaOH. In another embodiment, the other solvent is a hydrocarbon, such as hexane. In another embodiment, two, three or more extractions with different solvents may be performed on the post-distillation plant material. Alternatively or in combination, the plant material may be extracted two or more times with the same solvent.

Another aspect of the invention features a method for obtaining essential oil and one or more additional substances from plant material, comprising: (a) subjecting the plant material to water or steam distillation to obtain the essential oil, resulting in formation of post-distillation plant material; (b) contacting the post-distillation plant material with a solvent under conditions permitting extraction of the one or more substances from the plant material into the solvent; and (c) obtaining the one or more substances from the solvent. The plant material may be from a whole plant or any plant part, including one or more of flowers, seeds, leaves, stems and roots. In certain embodiments, the plant material is composed of stems and leaves, and in an exemplary embodiment, leaves are utilized.

The plant material can be from any plant from which essential oils are extracted, including but not limited to the genera and species set forth above.

Substances that can be isolated in accordance with this method include essential oils and, without limitation, any of the substances set forth above and/or described in detail in the specification and examples. In a particular embodiment, the method is adapted to favor extraction of phenolic compounds.

The solvent or solvent system can be of any type customarily used to extract substances such as those described herein from plant material. In one embodiment, the solvent is an alcohol. In a particular extraction the solvent is 80% ethanol. In embodiments utilizing a solvent that contains water, the method can further comprise removing the solvent from the water and extracting the remaining water with a different solvent, such as ethyl acetate.

In certain embodiments, the method further comprises extraction of the post-distillation plant material with another solvent. In one embodiment, the other solvent is a base, such as NaOH. In another embodiment, the other solvent is a hydrocarbon, such as hexane. In another embodiment, two, three or more extractions with different solvents may be performed on the post-distillation plant material. Alternatively or in combination, the plant material may be extracted two or more times with the same solvent.

Another aspect of the invention features a collection of one or more plant substances obtained in accordance with any of the above-described methods. In one embodiment, the collection is present in a dry residue formed after evaporation of the solvent(s). In another embodiment, the collection is present in the solvent used for extraction. In another embodiment, the collection is present in a different solvent or solvent system. The collection may comprise one or more of the substances listed hereinabove or throughout the specification. In exemplary embodiments, the plant material is oregano. In one embodiment, the collection includes one or more of pyrocatechol; 4-vinylphenol; 5,4'-dimethoxy-2-methylbibenzyl; 4-vinylguaiacol; syringol; 4-acetylanisole; 4-hydroxybenzaldehyde; vanillin; 2,1,3-benzothiadiazole; 3-hydroxyacetophenone; acetovanillone; acetoveratrone; syringaldehyde; and acetosyringone. In another exemplary embodiment, the collection includes one or more of syringic acid; diterpene; 2-isopropyl-5-methyl-hydroquinone; coumaric acid; ferulic acid; dihydrocaffeic acid; caffeic acid; rosmarinic acid; and various flavonoids. In another exemplary embodiment, the collection includes one or more of thymol; carvacrol; β-bisabolene; neophytadiene; thymoquinone; thymohydroquinone; phytol acetate; squalene; vitamin E; phytol; and (23S)-ethylcholest-5-en-3.beta.-ol.

Other features and advantages of the invention will become apparent by reference to the drawings, detailed description and examples that follow.

DETAILED DESCRIPTION OF ILLUSTRATIVE EMBODIMENTS

In accordance with various aspects of the present invention, methods are provided for obtaining substances of interest from plant material that has previously been subjected to water or steam distillation of essential oils. It has heretofore been the practice in the industry to discard the residual plant material after distillation of essential oils, on the assumption that no additional components of appreciable value could be obtained from such residual material. Contrary to this notion, it has been discovered in accordance with the present invention that a number of substances can indeed be retrieved from such plant material, many of which exhibit functional features, e.g., antioxidant properties, that are equivalent to those from substance isolated from plant material that has not been subjected to water or steam distillation.

The methods can be practiced on any plant. Suitable plants are those with at least one tissue or organ containing a substance or agent that is extractable by the methods set forth below, and from which essential oils may be obtained by water or steam distillation.

In certain embodiments, selected plant substances or agents (sometimes referred to herein as components) include phenolic compounds, flavones, isoflavones or other flavonoid compounds, glycosides, anthocyanins, proanthocyanidins and procyanidins and related compounds, catechins, terpenes, lignins, tannins, glucosinilates, aliphatic and cyclic organic acids, to name a few.

Suitable plants include, but are not limited to, angelica root, anise, balsam, basil, bay, bay laurel, beeswax, benzoin, bergamot, bergamot mint, bois-de-rose, boronia, cajeput, cardamum, carrot seed, cedarwood, chamomile, cinnamon, citronella, clary sage, clove bud, coriander, cypress, dill, elemi, eucalyptus (including lemon eucalyptus), fennel, fir needle, galbanum, geranium (including rose geranium), ginger, grapefruit, helichrysum, hyssop, immortelle, jasmine, juniper berry, kanuka, lavender, lavendin, lemon, lemongrass, lime, linden blossom, mandarin, manuka, marjoram, may chang, myrrh, myrtle (including lemon myrtle), neroli, niaouli, nutmeg, oakmoss, olibanum orange (bitter and sweet), oregano, palmarosa, parsley, patchouli, pepper (black, white, sweet or hot), peppermint and related mints, petitgrain pine, ravensara, rose, rosemary, rosewood, sandalwood, spearmint, spikenard, spruce, tangerine, tea tree (common, lemon, New Zealand), thyme, tobacco, tuberose, vanilla, vetiver, violet leaf, yarrow and ylang ylang. Typically, essential oil-producing plants from the Labiaceae, Umbelliferae and Compositae (Apiaceae) are suitable for use. In particular embodiments, the plants are from the mint family or other aromatic herbs, e.g., oregano and rosemary, to name a few. Particularly suitable plants include, but are not limited to, *Origanum* spp. (e.g., *O. syriacum*, *O. dayi*, *O. vulgare*, *O. onites*), *Mentha* spp. (e.g., *M. longifolia*, *M. spicata*, *M. piperita*) *Agastache*, *Ocimum* spp. (e.g., *O. basilicum*, *O. gratissimum*, *O. canum*, *O. americanum*), *Salvia* spp. (e.g., *S. officinalis*, *S. fruticosa*), *Artemisia* spp. (e.g., *A. dranunculus*, *A. judaica*, *A. aborescens*, *A. absinthum*), *Melissa officinalis*, *Achillea* spp. (e.g., *A. millenfolium*, *A. fragrantissimum*), *Thymus vulgare*, *Coridothymus capitatus*, *Micromeria fruticosa*, *Rosmarinus officinalis*, *Pelargonium graveolens* (geranium) and *Coleus* spp. In exemplary embodiments, mint (e.g., *Mentha spicata*, *M. piperita*), rosemary (*Rosmarinus officinalis*), oregano (*Origanum syriacum*, *O. dayi*, *O. vulgare*), thyme (*Thymus vulgare*), *Ocimum basilicum* and *Melissa officinalis* are used.

Any part of the plant from which essential oils are obtained are suitable for use in the present invention. These include, but are not limited to, flowers, seeds, bracts and other floral parts, stems, leaves and roots. In certain embodiments, leaves and stems are utilized. In other embodiments, leaves are utilized.

The method involves (1) obtaining residual plant material that has been subjected to water and/or steam distillation of essential oils, (2) contacting the plant material with a solvent under conditions permitting the extraction of the substance from the plant material into the solvent, and (3) obtaining the substances from the solvent. In a preferred embodiment, the solvent is a water-miscible organic solvent, such as an alcohol. Optionally, the plant residue can be subjected to one or more additional extractions with a different solvent system designed to release one or more other substances of interest from the plant material. In one exemplary embodiment, the residual material is subjected to a second extraction with NaOH, with optional heating, to release phenols from the cell wall. In another exemplary embodiment, the residue is extracted with a nonpolar solvent such as pentane, hexane, or heptane, the extract is evaporated to dryness and the dissolved solids are resuspended in a suitable medium, such as an oil. It will be understood by the skilled artisan that the plant material may be subjected to a drying step before and/or after the extraction(s), as would be customary practice.

In another embodiment involving more than one extraction, the extraction order can be reversed or, in the case of more than two extractions, the order of extractions can be changed. For instance, extraction with a nonpolar solvent may be performed before extraction with a polar or water-miscible solvent.

In another embodiment, the solvent containing the extracted plant substances can itself be subjected to further extraction. For example, plant material may be extracted with an aqueous alcohol, such as 80% ethanol. The alcohol may then be removed from the solvent, leaving water. The water may then be extracted with another solvent, such as ethyl acetate. Depending on relative solubility, some plant substances remain in the water phase while others partition to the other solvent phase.

Solvents suitable for use in the present invention include any solvent capable of extracting a selected component or substance, as described above, from the plant material. Particularly suitable solvents are those that are non-toxic or of limited toxicity. Examples of suitable solvents include, but are not limited to, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, tetrahydrofuran, sodium hydroxide, potassium hydroxide, ethyl acetate, vegetable oil, propylene glycol, neobe oil, glycerin, benzyl alcohol and triacetin. In a preferred embodiment, the solvent is food grade.

Other suitable solvents include, but are not limited to, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutylketon, methylcyclohexane, N-methylpyrrolidone, nitromethane, pyridine, sulfolane, tetralin, toluene, 1,1,2-trichloroethene and xylenes.

In a particular embodiment, phenolic compounds and other water-soluble substances are targeted for extraction. In this instance, a particularly suitable first extraction comprises contacting the post-distillation plant material with an aqueous alcohol, for example 80% ethanol. Subsequent extractions of the plant material can involve a base, such as sodium hydroxide, to liberate phenolics from the plant cell wall. Further extraction of the water after evaporation of the alcohol in the first solvent, e.g., using ethyl acetate, can further purify and concentrate phenolic compounds.

Another aspect of the invention features a system for recovering at least one essential oil and at least on other selected component from a plant. This method combines a typical water or steam distillation of the essential oil with a subsequent solvent extraction step, or combination of steps, as outlined above. This method involves the following basic steps: (1) performing a water and/or steam distillation on selected plant material, in accordance with standard methods known in the art, to obtain the essential oil(s), (2) after the distillation is complete, contacting the plant material with a solvent under conditions permitting the extraction of the substance from the plant material into the solvent, and (3) obtaining the substances from the solvent. In a preferred embodiment, the solvent is a water-miscible organic solvent, such as an alcohol. Optionally, the plant residue can be subjected to one or more additional extractions with a different solvent system designed to release one or more other substances of interest from the plant material. In one exemplary embodiment, the residual material is subjected to a second extraction with NaOH, with optional heating, to release phenols from the cell wall. In another exemplary embodiment, the residue is extracted with a nonpolar solvent such as pentane, hexane, or heptane, the extract is evaporated to dryness and the dissolved solids are resuspended in a suitable medium, such as an oil.

In another embodiment, the solvent containing the extracted plant substances can itself be subjected to further extraction. For example, plant material may be extracted with an aqueous alcohol, such as 80% ethanol. The alcohol may then be removed from the solvent, leaving water. The water may then be extracted with another solvent, such as ethyl acetate. Depending on relative solubility, some plant substances remain in the water phase while others partition to the other solvent phase.

As for the previous method, it will be understood by the skilled artisan that the plant material may be subjected to a drying step prior to the distillation, and/or before or after the extraction(s), as would be customary practice. It will also be understood that the solvent steps can be reversed or the order altered in the case of multiple extractions, if desired. Solvents suitable for this method are the same as those listed above for the previous method.

Another aspect of the invention features a collection of one or more plant substances obtained in accordance with either of the above-described methods. In one embodiment, the collection is present in a dry residue formed after evaporation of the solvent(s). In another embodiment, the collection is present in the solvent used for extraction. In another embodiment, the collection is present in a different solvent or solvent system.

As will be appreciated by one of skill in the art, the solvent system and extraction procedures that are selected will influence the content and amount of different substances extracted. Thus, depending on the plant material, the solvent system and the conditions used and for extraction, different extract profiles may be obtained. For instance, in exemplary embodiments utilizing oregano, an extraction with aqueous ethanol yielded a collection of 12-14 particular substances as set forth in Example 3, while a hexane extraction yielded an overlapping but not identical collection of substances.

The following examples are provided to describe the invention in greater detail. They are intended to illustrate, not to limit, the invention.

Example 1

Extraction of Post-Distillation Oregano Plant Material

For these processes, various parts of the oregano plant, e.g., leaves, stems, flowers, were utilized. In some of the procedures, plant parts were combined, while in other procedures they were treated separately. Oregano leaves were found particularly suitable. Plant material that had been previously subjected to water/steam distillation to remove essential oils were dried to about 7-10% moisture content and ground to a fine powder. The powder was mixed with 80% ethanol at a ratio of one part powder to ten parts solvent and placed on a rotary shaker at about 150 rpm for 12 hours at 20-25° C.

The solvent was separated from the plant residue by gravity or aspiration filtration. The ethanol was evaporated from the solvent under vacuum at 30° C., and the water containing the dissolved plant substances was retained.

As an optional step, the water fraction containing the plant substances was extracted with ethyl acetate by mixing the water fraction with ethyl acetate in a separatory funnel, then separating the phases from one another. This extraction was typically performed 2-4 times, and the ethyl acetate fractions were combined.

The plant residue was subjected to a second extraction by mixing with hexane. The hexane was separated from the plant residue by filtration. The solvent was evaporated to dryness and the dissolved solids were resuspended in oil. This process was repeated at least twice, but more typically 3-4 times, after which the hexane-extracted plant residue was discarded.

An alternative second extraction was employed in a different sample. The ethanol extracted plant residue was mixed with an excess of 1 M NaOH and incubated overnight at 60° C. The extract was then neutralized with HCl until the pH was 4.5. The liquid, which contained phenolic compounds associated with the cell wall, was separated from the plant residue by filtration. The plant residue was discarded.

The foregoing extraction procedures, including the ethanol extraction and, optionally, one of the additional extractions, have been performed on post-distillation plant material from the following species: *Mentha* spp. (e.g., *M. spicata*, *M. piperita*), *Rosmarinus officianalis*, *Origanum* spp. (e.g., *O. syriacum*, *O. dayi*, *O. vulgare*), *Ocimum basilicum*, *Thymus vulgare* and *Melissa officianalis*.

Example 2

Distillation of Essential Oils from *Mentha longifolia* and Extraction of Plant Material Plant Material Selected clones of *Mentha longifolia* L. were isolated from 25 wild-grown populations and transferred to an experimental field at Newe Ya'ar Research Center, Ramat Yishay, Israel. The plants were grown in local clay soil with drop irrigation. The agricultural practices utilized were those that have been described for other species of the Lamiaceae (Dudai et al., 1992 Physiologia Plantarum 84: 453-459). Leaves and stems from collected plants were dried at 40° C. for 72 hours, and were next ground in a coffee grinder just before extraction.

Essential Oil Distillation

Samples, weighing around 250 g of fresh plant material were hydro distilled for 1.5 h in a modified Clevenger apparatus. The essential oil was cooled and separated from the cohabited water (Dudai et al., 1992, supra).

Phenolic Acids Extraction, Analyses and Antioxidant Activity Extraction

1. Extraction of Phenolic Compounds in a Free Form (Extraction I).

Three hundred mg of ground *Mentha* sp. leaves and stems were mixed with 25 mL of 80% methanol in 50 mL tube. The tubes were shaken at 165 rpm overnight at room temperature. Next, 2 mL of the methanolic extract were placed in Eppendorf tube and spun in Eppendorf centrifuge for 5 minutes to remove particles before using it for analysis. The rest of the extract was kept in −20° C. for further analyses.

2. Extraction of Cell Wall-Bound Phenolic Compounds.

The supernatant from extraction I was used to estimate phenolics in the free form. The plant material, remaining after extraction was washed with 3 volumes of methanol and 3 volumes of acetone to wash-off residual free phenolics, or until reading of the washing solvent was nil at 280 nm, using Agilent 8453 UV-Visible spectrophotometer. Fifty mg of the solvent-washed and air-dried residue was placed in 2 mL Eppendorf tubes and mixed with 1 mL of 1 M NaOH. The tubes were incubated overnight at 60° C. Next, around 100 µL of 10 M HCl was added to neutralize the extract until the pH was 4.5. Then the tubes were centrifuged in an Eppendorf centrifuge for 5 minutes. The resulting supernatant, referred to as cell wall extract, was used to estimate wall-bound phenols.

3. Antioxidant Activity. Radical Scavenger Assay, using 1,1-diphenyl-2-picryldrazyl (DPPH).

The Radical Scavenger Assay was measured by monitoring the reduction of DPPH (Sigma, St. Louis, USA) in presence of either the mint leaf and stem tissue extract (representing phenolics in a free form), or the cell wall extract (representing wall-bound phenolic compounds). Measurements of antioxidant activity were carried out by spectroscopy, using Agilent 8453 UV-Visible spectrophotometer, as outlined below. Six mg of DPPH were mixed in 100 mL of 100% ethanol until it dissolved by vigorous mixing for 15 minutes. This reaction agent was made fresh for each new analysis. The purple color of a fresh non-reduced DDPH reagent, was adjusted to around $OD_{517}=1.0$. Ten µL of the mint extract, either free form or wall-bound, were placed in a dry Eppendorf tube. Then, 990 µL of the DPPH reagent were added. The mixture was incubated in the dark at room temperature for one hour, after which the absorbency of the DPPH-mint mixture was read at 517 nm. The obtained absorbency values were subtracted from the original base line reading of the original purple color at $OD_{517}=1.0$. Care was taken to read sample in a range of 0.3 to 0.6 at $OD_{517}$, in order to remain in a linear range. For this reason, some samples were diluted prior to the assay. A standard curve for chlorogenic acid (Sigma, St. Louis USA)-induced reduction of DPPH was performed under the same conditions as the mint extract. The antioxidant activity was then expressed as chlorogenic acid equivalent.

HPLC Analysis of Rosmarinic, Coumaric and Caffeic Acid

HPLC (Waters, USA) was used for the separation and estimation of phenolic acids. The methanolic mint leaf and stem tissue extract (representing phenolic compounds in free form) was used to analyze for rosmarinic acid content. The HPLC conditions were as follows:

C-18 Column (Sigma, St. Louis, USA), 250×4.6 mm, 5 µm particle size, at a flow rate of 1 mL/min. and injection volume of 20 µL. The amount of HPLC-eluted rosmarinic acid was calculated from a standard curve for rosmarinic acid between 0.05 to 0.5 mg/mL. Standard curve for caffeic and coumaric acid were between 0.01-0.1 mg/mL.

The elution protocol that was used for rosmarinic acid is described below in Table 1. The elution protocol for that was used caffeic and coumaric acid is described below in Table 2.

TABLE 1

HPLC elution protocol for rosmarinic acid
Solvent A Acetilonitrile
Solvent B 0.1% Phosphoric Acid
Absorbance at 330 nm

| Time (Minutes) | Flow rate | Solvent A (%) | Solvent B (%) |
|---|---|---|---|
| Initial | 1 cc/min | 94 | 6 |
| 8 | 1 cc/min | 84 | 16 |
| 20 | 1 cc/min | 40 | 60 |
| 25 | 1 cc/min | 40 | 60 |
| 25 | 1 cc/min | 6 | 94 |
| 35 | 1 cc/min | 94 | 6 |
| 40 | 1 cc/min | 94 | 6 |

TABLE 2

HPLC Elution Protocol for caffeic and coumaric acid
Solvent A Water with 1.25% Acetic Acid
Solvent B Methanol with 1.25% Acetic Acid
Absorbance at 280 nm

| Time (Minutes) | Flow rate | Solvent A (%) | Solvent B (%) |
|---|---|---|---|
| Initial | 1 cc/min | 85 | 15 |
| 10 | 1 cc/min | 85 | 15 |
| 20 | 1 cc/min | 80 | 20 |
| 30 | 1 cc/min | 80 | 20 |
| 45 | 1 cc/min | 50 | 50 |
| 55 | 1 cc/min | 85 | 15 |
| 60 | 1 cc/min | 85 | 15 |

In an alternative procedure, the above-recited protocol is performed on *M. longifolia* plant material that has been subjected to water/steam distillation.

Example 3

Comparison of Total Phenols and Antioxidant Activity in Oregano Extracts Before and after Distillation of Essential Oils, and Analysis of Extracts Plant Material Cultivated oregano (*Origanum vulgare*) was utilized. Prior to, or after distillation (depending on the treatment), plant material was dried to 7-10% moisture content and ground to a powder.

Essential Oil Distillation

About 2,000 kg field-dried oregano (40% moisture) was distilled in a 20 cubic meter container by a commercial steam distillation apparatus (Newhouse Manufacturing Co., Inc. Redmond, Oreg.). Samples of this material were utilized.

Phenolic Acids Extraction, Analyses and Antioxidant Activity Extraction

Extraction of Phenolic Compounds in a Free Form (Extraction I).

Two to three hundred mg of ground leaves and stems (either pre- or post-distillation) were mixed with 25-50 mL of 80% ethanol at about 150-165 rpm overnight at room temperature. Next, an aliquot of the ethanolic extract was placed in centrifuged for 5 minutes to remove particles before using it for analysis. The rest of the extract was kept in −20° C. for further analyses.

Next, an aliquot of the ethanolic extract was placed in centrifuged for 5 minutes to remove particles before using it for analysis. The rest of the extract was kept in −20° C. for further analyses.

NaOH Extraction of Cell Wall-Bound Phenolic Compounds.

The supernatant from extraction I was used to estimate phenolics in the free form. A portion of the plant material, remaining after ethanol extraction was washed with 3 volumes of ethanol and 3 volumes of acetone to wash off residual free phenolics, or until reading of the washing solvent was nil at 280 nm. Fifty mg of the solvent-washed and air-dried residue was placed in 2 mL Eppendorf tubes and mixed with 1 mL of 1 M NaOH. The tubes were incubated overnight at 60° C. Next, around 100 µL of 10 M HCl was added to neutralize the extract until the pH was 4.5. Then the tubes were centrifuged in an Eppendorf centrifuge for 5 minutes. The resulting supernatant, referred to as cell wall extract, was used to estimate wall-bound phenols.

Hexane Extraction of Additional Water-Insoluble Components.

A portion of the plant material remaining after ethanol extraction was dried, then mixed with hexane and incubated overnight on a rotary shaker at 150 rpm at 25° C. The hexane extract was separated from the plant material by filtration. This extraction process was repeated on the plant material 3-4 times, after which the hexane fractions were combined, the hexane evaporated, and the remaining material resuspended and prepared for GC-mass spectrometry in accordance with standard methods.

Antioxidant Activity. Radical Scavenger Assay, using 1,1-diphenyl-2-picryldrazyl (DPPH).

The Radical Scavenger Assay was measured by monitoring the reduction of DPPH (Sigma, St. Louis, USA) in presence of either the plant tissue extract (representing phenolics in a free form), or the cell wall extract (representing wall-bound phenolic compounds). Measurements of antioxidant activity were carried out by spectroscopy, as outlined below. Six mg of DPPH were mixed in 100 mL of 100% ethanol until it dissolved by vigorous mixing for 15 minutes. This reaction agent was made fresh for each new analysis. The purple color of a fresh non-reduced DDPH reagent, was adjusted to around $OD_{517}=1.0$. Ten µL of the mint extract, either free form or wall-bound, were placed in a dry Eppendorf tube. Then, 990 µL of the DPPH reagent were added. The mixture was incubated in the dark at room temperature for one hour, after which the absorbency of the DPPH-mint mixture was read at 517 nm. The obtained absorbency values were subtracted from the original base line reading of the original purple color at $OD_{517}=1.0$. Care was taken to read sample in a range of 0.3 to 0.6 at $OD_{517}$, in order to remain in a linear range. For this reason, some samples were diluted prior to the assay. A standard curve for chlorogenic acid (Sigma, St. Louis USA)-induced reduction of DPPH was performed under the same conditions as the plant extract. The antioxidant activity was then expressed as chlorogenic acid equivalent.

HPLC Analysis of Rosmarinic and Caffeic Acid

HPLC (Waters, USA) was used for the separation and estimation of phenolic acids. The ethanolic tissue extract (representing phenolic compounds in free form) was used to analyze for rosmarinic acid content. The HPLC conditions were as follows:

C-18 Column (Sigma, St. Louis, USA), 250×4.6 mm, 5 µm particle size, at a flow rate of 1 mL/min. and injection volume of 20 µL. The amount of HPLC-eluted rosmarinic acid was calculated from a standard curve for rosmarinic acid between 0.05 to 0.5 mg/mL. The standard curve for caffeic acid was between 0.01-0.1 mg/mL.

The elution protocol for rosmarinic acid was the same as that described above in Example 2, Table 1. The elution protocol for caffeic acid was the same as that described above in Example 2, Table 2.

The ethanolic extract (extract I) and hexane extract were also analyzed by GC-mass spectrometry in accordance with standard methods, to identify principal components.

Results:

Total phenolics and antioxidant activity in the ethanol extracts (free phenolics) and NaOH extracts (cell wall material) of pre-distillation and post-distillation plant material was measured, and the results are presented in Table 3.

TABLE 3

| | Sample | Antioxidants (Chlorogenic acid equivalent mg/g DW) | | Total Phenolics (Chlorogenic acid equivalents mg/g DW) | |
|---|---|---|---|---|---|
| | | EtOH | EtOH/NaOH | EtOH | EtOH/NaOH |
| Post-distillation | 1 | 68.33 | 25.14 | 7.95 | 6.87 |
| | 2 | 74.47 | 26.27 | 7.78 | 7.27 |
| Pre-distillation | A | 141.45 | 18.25 | 15.43 | 2.63 |
| | B | 128.95 | 14.17 | 11.43 | 2.18 |
| | C | 130.42 | 17.15 | 12.43 | 1.91 |

Amounts of rosemarinic acid (RA) in the ethanol extracts (free phenolics) and ethanol followed by NaOH extracts (cell wall material) and caffeic acid (CAF) in the ethanol followed by NaOH extracts of pre-distillation and post-distillation plant material was measured, and the results are presented in Table 4.

TABLE 4

| | | EtOH extract | | EtOH/NaOH extract |
|---|---|---|---|---|
| | Sample | Rosmarinic Acid (% DW) | Caffeic Acid (% DW) | Caffeic Acid (% DW) |
| Post-distillation | 1 | 0.55 | 1.33 | 2.16 |
| | 2 | 0.57 | 1.38 | 2.49 |
| Pre-distillation | A | 1.25 | 1.40 | 0.33 |
| | B | 3.27 | 1.43 | 1.01 |
| | C | 3.35 | 1.30 | 0.66 |

The ethanol extract of post-distillation oregano plant material was subjected to GC-mass spectrometry and HPLC-mass spectrometry to identify compounds. GC-MS analysis of one sample identified the following compounds: pyrocatechol; 4-vinylphenol; 5,4'-dimethoxy-2-methylbibenzyl; 4-vinylguaiacol; syringol; 4-acetylanisole; 4-hydroxybenzaldehyde; vanillin; 2,1,3-benzothiadiazole; 3-hydroxyacetophenone; acetovanillone; acetoveratrone; syringaldehyde; and acetosyringone. GC-MS analysis of another sample identified the following compounds: 3-hydroxyacetophenone; 4-acetylanisole; 4-hydroxybenzaldehyde; 4-vinylguaiacol; acetosyringone; pyrocatechol; 4-vinylphenol; acetovanillone; acetoveratrone; syringaldehyde; syringol; and vanillin. HPLC-MS analysis of another sample identified the following compounds: syringic acid; diterpene; 2-isopropyl-5-methyl-hydroquinone; coumaric acid; ferulic acid; dihydrocaffeic acid; caffeic acid; rosmarinic acid; and various flavonoids.

The hexane extract of ethanol-extracted post-distillation plant material was subjected to GC-mass spectrometry to identify compounds. GC-MS analysis of two different samples identified the following compounds: thymol; carvacrol; β-bisabolene; neophytadiene; thymoquinone; thymohydroquinone; phytol acetate; squalene; vitamin E; phytol; and (23S)-ethylcholest-5-en-3.beta.-ol.

Example 3

Comparison of Total Phenols and Antioxidant Activity in Rosemary Extracts Before and after Distillation of Essential Oils Cultivated rosemary (*Rosmarinus officianalis*) plant material (leaves and stems) was subjected to ethanol extraction either before or after distillation of essential oils, utilizing the methods described in Example 2. Total phenolics and antioxidant activity in the extracts were measured, and results are presented in Table 5.

TABLE 5

| | Antioxidants (Chlorogenic acid equivalents mg/g DW) | Total Phenolics (Chlorogenic acid equivalents mg/g DW) |
|---|---|---|
| Post-distillation | 175.2 | 18.99 |
| Pre-distillation | 146.9 | 15.33 |

As can be seen, in this instance, the recovery of phenolics and antioxidant materials was greater from the post-distilled material than from the pre-distilled material. Without being limited to any particular underlying mechanism, one explanation for this result is that the distillation process itself caused a partial release of these substances, rendering them more available to extraction by ethanol.

The present invention is not limited to the embodiments described and exemplified above, but is capable of variation and modification within the scope of the appended claims.

What is claimed:

1. A method for obtaining one or more substances from plant material, comprising:
    (a) providing post-distillation plant material from which essential oils have been removed by water or steam distillation;
    (b) contacting the post-distillation plant material with a first solvent under conditions permitting extraction of at least one of the one or more substances from the plant material into the first solvent, wherein the first solvent is a polar solvent, thereby producing a first extract and a polar solvent-extracted plant material;
    (c) separating the first extract from the polar solvent-extracted plant material;
    (d) contacting the polar solvent-extracted plant material with a second solvent, which is different from the first solvent, under conditions permitting extraction of at least another one of the one or more substances from the polar solvent-extracted plant material into the second solvent, thereby producing a second extract; and
    (e) obtaining the one or more substances from the first extract or the second extract, or from the first extract and the second extract.

2. The method of claim 1, wherein the plant material comprises one or more of flowers, seeds, leaves, stems and roots.

3. The method of claim 1, wherein the one or more substances is selected from phenolic compounds, flavones, isoflavones, glycosides, anthocyanins, proanthocyanidins, procyanidins, catechins, terpenes, lignins, tannins, glucosinilates, aliphatic and cyclic organic acids.

4. The method of claim 3, wherein the one or more substances has antioxidant activity.

5. The method of claim 1, wherein the plant material is from a plant genus selected from *Origanum, Mentha, Agas-* tache, *Ocimum, Salvia, Artemisia, Melissa, Achillea, Thymus, Coridothymus, Micromeria, Rosmarinus, Pelargonium* and *Coleus*.

6. The method of claim 5, wherein the plant material is from *Mentha spicata, Mentha piperita, Rosmarinus officinalis, Origanum syriacum, Origanum dayi, Origanum vulgare, Thymus vulgare, Ocimum basilicum* or *Melissa officinalis*.

7. The method of claim 1, wherein the first or second solvent is an alcohol.

8. The method of claim 7, wherein the first or second solvent is 80% ethanol.

9. The method of claim 1, wherein the first or second solvent is NaOH.

10. The method of claim 1, wherein the second solvent is hexane.

11. The method of claim 8, further comprising removing the ethanol from the first or second extract and extracting the remaining water with ethyl acetate to produce an ethyl acetate extract.

12. The method of claim 1, wherein the step of providing the post-distillation plant material comprises subjecting plant material to water or steam distillation to separate the essentials oil from the plant material, thereby producing the post-distillation plant material to be provided.

13. A method for obtaining a plurality of substances from plant material of genus *Origanum*, comprising:
  (a) providing post-distillation plant material of the genus *Origanum* from which essential oils have been removed by water or steam distillation;
  (b) contacting the post-distillation plant material with alcohol or an aqueous alcohol mixture under conditions permitting extraction of the one or more substances from the plant material into the alcohol or aqueous alcohol mixture, thereby producing an alcohol extract and alcohol-extracted plant material;
  (c) separating the alcohol extract from the alcohol-extracted plant material;
  (d) extracting the alcohol-extracted plant material with a solvent selected from NaOH and hexane, thereby producing a second extract; and
  (e) obtaining the plurality of substances from the alcohol extract or the second extract, or from the alcohol extract and the second extract.

14. The method of claim 13, wherein the plant material comprises one or more of flowers, seeds, leaves, stems and roots.

15. The method of claim 13, wherein the step of providing the post-distillation plant material comprises subjecting plant material to water or steam distillation to separate the essentials oil from the plant material, thereby producing the post-distillation plant material to be provided.

16. The method of claim 13, wherein the substances are selected from phenolic compounds, flavones, isoflavones, glycosides, anthocyanins, proanthocyanidins, procyanidins, catechins, terpenes, lignins, tannins, glucosinilates, aliphatic and cyclic organic acids.

17. The method of claim 15, wherein at least one of the substances has antioxidant activity.

18. The method of claim 17, wherein the plant material is from *Origanum syriacum, Origanum dayi*, or *Origanum vulgare*.

19. The method of claim 13, wherein the alcohol is ethanol.

20. The method of claim 13, wherein the aqueous alcohol mixture comprises 80% ethanol.

21. The method of claim 20, further comprising removing the ethanol from the extract and extracting the remaining water with ethyl acetate.

22. The method of claim 13, wherein step (d) comprises extracting the alcohol-extracted plant material with NaOH, thereby producing a NaOH extract.

23. The method of claim 13, wherein the NaOH is 1M NaOH.

* * * * *